US00PP16091P3

(12) United States Plant Patent
Hofmann

(10) Patent No.: US PP16,091 P3
(45) Date of Patent: Nov. 1, 2005

(54) **NEW GUINEA *IMPATIENS* PLANT NAMED 'FISUPNIC FLAME'**

(50) Latin Name: *Impatiens hawkeri*
Varietal Denomination: Fisupnic Flame

(75) Inventor: Birgit C. Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 42 days.

(21) Appl. No.: 10/829,218

(22) Filed: Apr. 22, 2004

(65) Prior Publication Data

US 2004/0216203 P1 Oct. 28, 2004

(30) Foreign Application Priority Data

Apr. 22, 2003 (CH) ..... 03-1997

(51) Int. Cl.[7] ..... A01H 5/00
(52) U.S. Cl. ..... Plt./318
(58) Field of Search ..... Plt./318

(56) References Cited

U.S. PATENT DOCUMENTS

PP11,486 P * 8/2000 Trees ..... Plt./318
PP13,180 P2 * 11/2002 Strope ..... Plt./318
PP13,700 P2 * 4/2003 Hofmann ..... Plt./318
PP13,711 P2 * 4/2003 Hofmann ..... Plt./318
PP13,996 P2 * 7/2003 Strope ..... Plt./318
PP14,694 P2 * 4/2004 Hofmann ..... Plt./318
2002/0174469 P1 * 11/2002 Strope ..... Plt./318
2004/0216203 P1 * 10/2004 Hofmann ..... Plt./318

OTHER PUBLICATIONS

UPOV ROM GTITM Computer Database, GTI Jouve Retrieval Software 2004/06 Citations for 'Fisupnic Flame'.*

* cited by examiner

*Primary Examiner*—Howard J. Locker
*Assistant Examiner*—W. C. Haas

(74) *Attorney, Agent, or Firm*—Foley & Lardner, LLP

(57) ABSTRACT

A new and distinct cultivar of New Guinea *Impatiens* plant named 'Fisupnic Flame', particularly characterized by the combined features of brilliant, orange-red flower color; large, butterfly-shaped flowers; dark green foliage, elliptical leaves; moderately tall plant habit; and beginning of flowering in mid season.

1 Drawing Sheet

Botanical description: *Impatiens hawkeri.*
Variety denomination: 'Fisupnic Flame'.

BACKGROUND OF THE INVENTION

The present invention comprises a new and distinct cultivar of New Guinea *Impatiens* plant, botanically known as *Impatiens hawkeri*, and hereinafter referred to by the cultivar name 'Fisupnic Flame'.

'Fisupnic Flame' is a product of a planned breeding program and originated from a hybridization made by the inventor, Birgit C. Hofmann, in a controlled breeding program in Hillscheid, Germany, in 2000.

The female parent was the variety 'Fisimp 102' (U.S. Plant Pat. No. 13,700), characterized by orange-red colored flowers, medium to late flowering response, medium green foliage, and fairly tall plant habit.

The male parent was the variety 'Fisimp 149' (U.S. Plant Pat. No. 13,711), having deep pink colored flowered with a red-purple center, dark green foliage, and about medium sized plant habit.

'Fisupnic Flame' was discovered and selected as one flowering plant within the progeny of the stated cross by the inventor in April, 2001 in a controlled environment in Galdar, Gran Canaria, Spain.

The first act of asexual reproduction of 'Fisupnic Flame' was accomplished when vegetative cuttings were taken from the initial selection in July, 2001 in a greenhouse in Galdar, Gran Canaria, Spain, by, or under the supervision of the inventor.

Horticultural examination of plants grown from these cuttings initiated in the spring of 2002 in Hillscheid, Germany, and continuing thereafter, has demonstrated that the combination of characteristics as herein disclosed for 'Fisupnic Flame' are firmly fixed and are retained through successive generations of asexual reproduction. The new cultivar reproduces true to type.

'Fisupnic Flame' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under green house conditions which approximate those generally used in commercial practice.

BRIEF SUMMARY OF THE INVENTION

The following traits have been repeatedly observed and are determined to be basic characteristics of 'Fisupnic Flame', which in combination distinguish this *Impatiens* as a new and distinct cultivar:

1. brilliant, orange-red flower color;
2. large, butterfly-shaped flowers;

3. dark green foliage, elliptical leaves;
4. moderately tall plant habit; and
5. beginning of flowering in mid season.

Of the many commercial cultivars known to the inventor, the most similar in comparison to "Fisupnic Flame" are the parental variety, 'Fisimp 102', and 'Fisnics Flame' (U.S. Plant Pat. No. 14,694).

In comparison to 'Fisimp 102', 'Fisupnic Flame' has a roughly similar flower color, a somewhat earlier flowering response, darker green foliage with reddish lower side, while 'Fisimp 102' has medium green foliage with light green underside.

In comparison to 'Fisnics Flame', 'Fisupnic Flame' has a somewhat lighter hue of flower color, and either flat or butterfly shaped flowers, not cup-shaped like those of 'Fisupnic Flame'. Additionally, 'Fisupnic Flame' is more floriferous, its leaves are somewhat narrower than leaves of 'Fisnics Flame', and its plant habit is more even and dense than with plants of 'Fisnics Flame'.

BRIEF DESCRIPTION OF THE DRAWING

The accompanying photographic drawing shows typical flower and foliage characteristics of 'Fisupnic Flame' with colors being as true as possible with illustrations of this type. The photographic drawing shows a side view of a typical flowering plant of 'Fisupnic Flame'.

DETAILED BOTANICAL DESCRIPTION

In the following description color references are made to The Royal Horticultural Society Colour Chart (R.H.S.). The color values were determined indoors from plants growing in a green-house in May 2003, Hillscheid, Germany.

The description is based on plants which were planted as rooted cuttings in 12 cm pots in late February 2003, and then grown in the greenhouse at a minimum temperature of 16° C. Most observations and measurements were made after the beginning of flowering in mid May, when the plants were about 12 weeks old.

PLANT

General appearance and form:

*Plant habit.*—Relatively tall, uniformly rounded, and well-branched; growth is indeterminate, though weak after beginning of flowering.

*Height.*—19.0 cm.

*Width.*—32.2 cm.

*Number of branches.*—12.

*Internode length.*—4.5 to 6.5 cm.

*Length of branches.*—15 to 18 cm.

*Diameter of branches.*—7 to 9 mm.

Stem color: Olive-green, reddish infused, the resulting color value near RHS 182 C.

Propagation: Usually terminal vegetative shoot tips for cuttings.

*Rooting.*—Roots initiate in about 18 days at 22° C., from sticking to transplanting.

*Cultivation time.*—Approximately 10 weeks of growing time to produce a marketable flowering plant in a 12 cm pot.

Foliage:

*Leaf arrangement.*—Primarily in whorls.

*Shape of leaf.*—Elliptic to narrow ovate, with acute base and acute to acuminate tip, surface glossy and somewhat rugose.

*Margin.*—Slightly serrated, ciliated.

*Leaf length.*—11.5 cm.

*Leaf width.*—4.7 cm.

*Upper surface, main color.*—Dark green, uniform, no variegation; mature leaves near RHS 139 A; young leaves near RHS 139 A.

*Veins on upper surface, color.*—Dark red, RHS 53A to 53B.

*Lower surface, color.*—Mature leaves are marbled, green and dull red, RHS 138 B and 184 C; Young leaves are RHS 187 D. Veins on lower surface color — RHS 185 A.

*Petiole.*—2.5 to 3.0 cm in length, 3 mm in diameter.

*Petiole, color.*—Upper side dark-red, RHS 53 A, lower side RHS 185 A.

Inflorescence:

*Flowering response.*—9 to 10 weeks after planting of rooted cuttings.

*Flowering season.*—Generally indeterminate, mainly from March to October, depending on light intensity.

Flower:

*Number of flowers per node.*—6 to 9, in various stages of development.

*Form of corolla.*—Single-type, 5 petals.

*Shape of corolla.*—Nearly round, large, with the petals overlapping, almost flat or butterfly-shaped.

*Diameter of corolla.*—Average length: 75 mm. Average width: 70 mm. Depth: 10 mm.

*Shape of petals.*—Cordate, shallow lobes at the top end, base attenuate. Top petal: 33 mm long, 58 mm wide. Lateral petals: 30 mm long, 37 mm wide. Lower petals: 33 mm long, 41 mm wide. Texture: Smooth, velvety. Aspect: Flat or slanting upright, upper petal may be slightly curved.

*Color (general tonality from a distance of three meters).*—Brilliant orange-red, with a small purple eye.

*Color of upper surface.*—RHS 44 B, no markings.

*Color of eye zone.*—Weak, RHS 61 B.

*Color of lower surface.*—RHS 40 A.

*Spur.*—Downwardly curved; 56 mm long; 3 mm in diameter; color pink, RHS 63 B.

*Peduncle color.*—Light green, RHS 145 B, pink near the flower end, RHS 48 B.

*Peduncle length.*—72 mm.

*Flower bud.*—Ovoid shape, 24 cm in length, 17 mm in width; color RHS 43 A.

Reproductive organs:

*Stamens.*—5 in number, fused.

*Anthers.*—Fused, hooded.

*Pollen.*—Whitish-yellow, about RHS 8 D.

*Style and stigma.*—Five in number, very short, reddish, about RHS 53 C.

*Ovary.*—5-celled, 5 mm long, surface color deep brown, RHS 187 B.

Disease/pest resistance/susceptibility: No observations to date.

I claim:

1. A new and distinct New Guinea *Impatiens* Plant named Fisupnic Flame as described and illustrated herein.

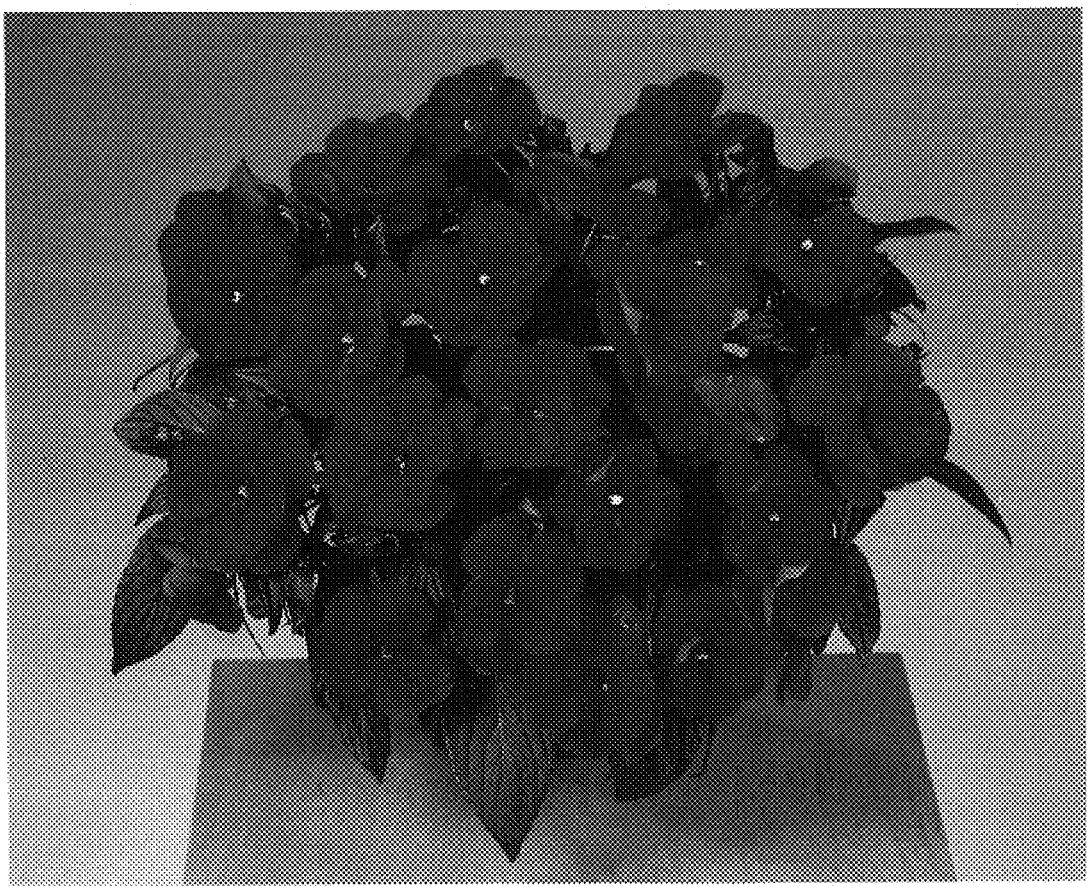

* * * * *